United States Patent
Li

(10) Patent No.: US 9,211,308 B2
(45) Date of Patent: Dec. 15, 2015

(54) EJACULUM OF ANIMALS AS MEDICINAL MATERIAL AND USES THEREOF IN MEDICAMENTS FOR TREATMENT OF DISEASES SUCH AS TUMORS, DEPRESSION, ETC

(75) Inventor: Yan Li, Xi'an (CN)

(73) Assignee: Hui Cheng (CN)

( * ) Notice: Subject to any disclaimer, the term of this patent is extended or adjusted under 35 U.S.C. 154(b) by 1310 days.

(21) Appl. No.: 12/598,189

(22) PCT Filed: Mar. 24, 2008

(86) PCT No.: PCT/CN2008/000573
§ 371 (c)(1),
(2), (4) Date: Jan. 14, 2010

(87) PCT Pub. No.: WO2008/134919
PCT Pub. Date: Nov. 13, 2008

(65) Prior Publication Data
US 2010/0189803 A1 Jul. 29, 2010

(51) Int. Cl.
*A61K 35/52* (2015.01)
*A61K 9/19* (2006.01)

(52) U.S. Cl.
CPC .. *A61K 35/52* (2013.01); *A61K 9/19* (2013.01)

(58) Field of Classification Search
CPC ................................. A61K 35/52; A61K 9/19
USPC ........................................................ 424/561
See application file for complete search history.

(56) References Cited

U.S. PATENT DOCUMENTS

| | | | |
|---|---|---|---|
| 4,342,789 A * | 8/1982 | Ueno et al. ..................... | 426/266 |
| 2002/0136757 A1 * | 9/2002 | Baron et al. .................. | 424/443 |

FOREIGN PATENT DOCUMENTS

| | | |
|---|---|---|
| CN | 1076598 A | 9/1993 |
| CN | 1126075 A | 7/1996 |

OTHER PUBLICATIONS

English Machine Translation of CN1076598.*
English Machine Translation of CN1126075.*
Liu et al., Freeze-dried sperm fertilization leads to full-term development in rabbits, Biology of Reproduction, vol. 70, p. 1776-1781, 2004.*
Family Medicine, 2003, No. 6, Zhang Kuiyi, "Effects of ejaculum", p. 20.

* cited by examiner

*Primary Examiner* — Taeyoon Kim
*Assistant Examiner* — Tiffany Gough
(74) *Attorney, Agent, or Firm* — Harness, Dickey & Pierce, P.L.C.

(57) ABSTRACT

Provided are ejaculum of animals as medicinal materials and uses thereof in manufacture of medicaments for treatment of various tumors, depression, senile dementia, and dermatosis. Said tumors include ovarian cancer, uterine cancer, breast cancer, esophageal cancer, stomach cancer, colon cancer, lung cancer, osteocarcinama, etc. The present medicinal material, alone or in combination with additional agents, is similar to cyclophosphamide in antineoplastic effects, which is accepted presently the most potent chemotherapeutic agent. It can inhibit the growth of tumors, not destroying the normal immune system of human. The present medicinal material of ejaculum is powdery crystal prepared by vacuum lyophilization from fresh ejaculum of animals, and it is suitable to a variety of dosage forms such as capsule or oral solution.

2 Claims, No Drawings

EJACULUM OF ANIMALS AS MEDICINAL MATERIAL AND USES THEREOF IN MEDICAMENTS FOR TREATMENT OF DISEASES SUCH AS TUMORS, DEPRESSION, ETC

FIELDS OF THE INVENTION

The invention relates to a method of manufacturing medicinal materials of animal extracts and use of animal extracts in the manufacture of medicaments for treating brain tumor, gynecological tumor, liver tumor, depression, Alzheimer's disease, blood disease, dermatosis, lupus erythematosus and other diseases.

BACKGROUND OF THE INVENTION

Cancers are known to be the leading factor of mortality among all diseases. They cause 1.6 million deaths in China per year, and there are 7 millions of people suffering from cancers per year the entire world. Despite the developments of medicaments and methods for treating cancers, the incidence and mortality of cancers are keeping increasing even in developed countries. Cancer is due to abnormal propagation of body cells. During the development of cancer lump, propagating cells consume a large amount of nutrients in the body and destroy the immune system, leading to body dysfunction and ultimately to death. Etiology and pathogenesis of cancer has not yet fully elucidated up to now. Conventional therapies for cancers include surgery excision, chemotherapy, radiation therapy and enantiopathy. They can have a certain therapeutic effect on the treatment of cancer, making some patients' conditions be temporarily improved, but recurrence and metastasis of the cancer often occur after a period of time. Meanwhile, some normal tissue cells and the immune system have been inevitably and greatly damaged in this process, which causes an unbearable suffering to the patient, including, for example, loss of appetite, pain, urine disorders, fever, hematemesis, and depressive and insomnia. Thus the quality of life was severely impaired. After a number of conventional radiotherapy and chemotherapy, patients will experience hair loss, skinny, and eating disorders. Therefore, many patients die of radiotherapy, chemotherapy and surgery rather than cancer. When these defects of conventional therapies become increasingly apparent, researchers began to turn to other strategies such as genetic therapies and immunological therapies, and so on. However, there is not a breakthrough yet now.

SUMMARY OF THE INVENTION

The purpose of the instant invention is to overcome the existing disadvantages of conventional therapies and to provide a medicinal material useful for treatment of brain tumor, gynecological tumor, liver tumor, depression, Alzheimer's disease, blood diseases, dermatosis, lupus erythematosus and other diseases. Furthermore, the medicinal material of the invention can avoid a variety of side-effects occurred in the treatment, and can participate in the preparations of many other useful medicaments.

It is well known that the ejaculum contains sperm. 95% by weight of the ejaculum is water, and the others ingredients include proteins, fructose, prostaglandins, vitamins, phospholipids and the like. Minerals, including calcium, potassium, phosphorus, magnesium and zinc, are also constituents. Animal proteins are all high-calorie food. The ejaculum also contains ascorbic acid (vitamin C), cholesterol, choline, blood group antigens, inositol, purines, pyrimidines, vitamin B12 and the like. Besides these nutrients, the ejalucum may also contains some mysterious materials which have not been identified. Analysis results, medical reports and clinical practice have confirmed that the ejaculum from human and animal have no any toxicity or side effect. Oral administration (or so-called "swallow") of the ejaculum has been used for the purpose of health care, but these administrations are based on fresh liquid ejaculum. This form of ejaculum is difficult to be long-term preserved and also difficult to be orally ingested. Furthermore, this form of ejaculum is difficult to be formulated into a medicament, or cannot be formulated into new pharmaceutical compositions with other ingredients. In addition to the same limitations in the formulation and storage as ordinary medicaments, the greatest obstacle of oral administration of the ejaculum is psychologically unacceptance of the oral ingestion of the ejaculum. This greatly limits the medical use of ejaculum as an effective medicament.

In order to solve these problems, based on many years researches, the invention provides a medicinal material of animal ejaculum which is suitable for oral administration alone or for the formulation of a pharmaceutical composition. The medicinal material is in the form of white powder prepared by vacuum lyophilization of the fresh animal ejaculum and suitable for being formulated into various dosage forms such as capsules or oral liquid and the like. The examples of animal ejaculum which can be used include the ejaculum of cattle, horses, donkeys and the like.

The animal ejaculum of the invention can be prepared by vacuum lyophilization using conventional vacuum lyophilizers. The fresh sterile liquid ejaculum can be placed in the vacuum lyophilizer after the removal of floccule, and dry powder form of ejaculum can be obtained by removal of water at the appropriate low temperature and vacuum. Lyophilization is a drying technology by use of the process of sublimation. Rapidly-frozen ejaculum is evaporated in a vacuum environment, so that water in solid form is sublimated into gas form and can be removed. Ejaculum in dry form thus can be obtained. Typically, the working pressure of the drying carbinet of the lyophilizer was set to 50 Pa, and the working temperature of the water catcher is $\leq -40°$ C. The traditional drying process without lyophilization will destroy sperm cells and lead to loss of the active ingredients. Only with a appropriate lyophilizing process, the chemical composition of ejaculum can be maintained, keeping the ejaculum composition unbroken and the biological activities of the products intact. The obtained dry powder of ejaculum can be stored in a sterile desiccator in vacuum and at room temperature. The implementation of this lyophilizing process is within the range of knowledge and abilities of the persons skilled in the art by making reference to the disclosure of the invention.

The inventor firstly and uniquely prepared lyophilized powder of ejaculum by using the lyophilization process above. The powder dosage form of ejaculum has potent anti-cancer activity and medical value. It has the same nutrient composition and therapeutic effect as fresh ejaculum. Furthermore, this dosage form has the advantages of simplicity and safety, as it is suitable for long-time storage with the period of validity of at least six months.

The medicinal material of the invention prepared by this method is easy to be oral administrated as it has no unfavorable flavors and will not cause any discomfort to the patients. The medicinal material of the invention is suitable for most of the patients in need thereof, and it exhibited unexpected therapeutic effects in manufacture of medicaments for treating various disease, for example, including brain tumor, gynecological tumor (e.g. ovarian cancer, uterine cancer and breast cancer), tumors in respiratory and digestive systems, liver tumor, depression, Alzheimer's disease, blood diseases, dermatosis, lupus erythematosus, etc.

The experimental data has shown that animal ejaculum, alone or in combination with additional medicinal materials, exhibits excellent effects in the treatment of a variety of diseases.

As shown by clinical practice, the capsule of ejaculum dry power of the present invention has many advantages as comparing to the conventional chemotherapeutical agents, including: 1) it can kill the tumor cells while do not damage normal cells; 2) it can prevent the metastasis of the cancer; 3) it has significant analgesic effects; and has no any undesirable side effect. In a large amount of clinical cases, patients were continuously administrated the dosage form of the invention for more than two years, and no undesirable effect was observed. 4) As most of conventional dosage forms of anticancer agents are injectable solutions and have great adverse effects, many patients may terminate the treatment and finally died for they could not tolerate any more. In contrast, the dosage form of the invention which is in the form of capsule or oral solutions has the advantages of ease of administration and more cost-effective.

THE DETAIL DESCRIPTION OF THE INVENTION

In order to facilitate oral administration and carriage, the lyophilized powder of ejaculum of the invention can be formulated into various dosage forms such as soft capsules, oral solutions, hard capsules and the like. The lyophilized powder of ejaculum of the invention can also be formulated with additional agents to prepare other new medicaments. The lyophilized powder of ejaculum of the invention can be simply dissolved in water to prepare an oral solution. In order to improve the flavor or taste, some additives such as erythorbate can be added.

The animal pharmacodynamics has shown that the lyophilized powder of ejaculum of animals, alone or in combination with additional medicinal materials, exhibits excellent effects on treatment of a wide variety of cancers. The comparison of therapeutic effects is as follows.

EXAMPLES

1. Animal Test

The mice inoculated by $S_{180}$ tumor cells (mouse sarcoma) were used as model animals. The inoculated mice were divided into following three groups:
1) treatment group: treated by oral administration of capsules containing lyophilized powder of ejaculum of cattle as main active ingredients (XINXING No. I), and the administration is carried out three times per day and 3 g per dose for three months: 0.3 ml/10 g body weight/day×10, stomach lavage;
2) positive control group: treated by cyclophosphamide, which is a widely accepted chemotherapeutic agent: 0.3 ml/10 g body weight/day×10, stomach lavage; and
3) negative control group: treated by distilled water: 0.5 ml/mouse×10, stomach lavage.

In the meantime, non-inoculated mice were feed and used as the native control group.

The results were summarized in Table below.

| The therapeutic effects of "XINXING No. I" on mice sarcoma $S_{180}$ | | | | |
|---|---|---|---|---|
| item | Treated group | Positive control | Negative Control | Native control |
| Weight of Tumor (g) (X ± SD) | 0.760 ± 0.269 (n = 9) | 0.614 ± 0.268 (n = 8) | 1.858 ± 0.522 (n = 9) | |
| Mice body (GPT) | 71.4 ± 31.9 | 39.2 ± 5.69 | 114.2 ± 44.4 | 30.5 ± 9.38 |

As shown in the above table, the medicament of the invention, XINXING No. I exhibited similar antineoplastic effects as cyclophosphamide. Furthermore, the constitutions of mice of treatment group are shown to be much stronger than those of positive control group, indicating that the medicaments of the invention can inhibit the growth of tumors, while not destroy the normal immune system of the organism.

From the photograph of the results, it can be seen that the tumors were reduced by the treatment according to the present invention.

These experiments were performed in the laboratory of Biochemistry Institute of former XI'AN Medical University, and the detail experimental reports including photographs can be submitted upon the requirement.

2. Clinical Test

1) Since 1992, about ten thousands cancer patients (most of them are patients with metastasis and recurrence of cancer after the surgery, radiotherapy or to chemotherapy) have been treated with the formulation "XINXING No. I" according to the invention, which contains lyophilized powder of animal ejaculum as main active ingredients. The overall response rate was 94% (with improved clinical symptoms, reduced pain, increased food intake, and improved mental performance), effective rate was 56% (with significantly alleviated clinical symptoms, and effectively controlled and reduced tumor lump), the cure rate was 11% (no malignant cells were monitored by biopsy and the patients have a healthy life like healthy adult). According to randomized statistic results of 160 cases of breast cancer patients, the response rate was 95%, the effective rate was 57%, and the cure rate was 11%. According to randomized statistic results of 26 cases of depression patients, the response rate was 93%, the effective rate was 53%, and the cure rate was 12%. According to statistic results of 15 cases of lupus erythematosus patients, the response rate was 95%, the effective rate was 55%, and the cure rate was 11%. According to statistic results of 30 cases of Alzheimer's disease patients, the response rate was 62%, the effective rate was 49%, and the cure rate was 10%. The results of brain tumor treatment were: the response rate of 89%, the effective rate of 57%, and the cure rate of 14%. The results of liver tumor treatment were: the response rate of 93%, the effective rate of 55%, and the cure rate of 10%. The results of lung cancer treatment were: the response rate of 91%, the effective rate of 63%, and the cure rate of 14%.

The clinical results have shown that after a period of treatment by the medicaments of the present invention, the majority of cancer patients can exhibit improved subjective symptoms, such as reduced pain, increased appetite, improved sleep and mental performance. More specific results of the clinical and pharmacological research can always be submitted upon the requirement.

2) The medicament of the invention has a great advantage of broad spectrum of applicability. It can be significantly effective not only in the treatment of the disease of digestive and respiratory system, but also in the treatment of blood diseases or osteocarcinama.

3) The dry power of ejaculum of the invention is suitable to be formulated into medicaments. As shown in research results, the lyophilized powder of ejaculum of the invention is suitable to be formulated with other medicinal materials to prepare a compound medicine, which has better therapeutic effects on many diseases. For example, a kind of compound anti-cancer capsule ("FUFANG JINGLING XIAOLIU JIAONANG"), which contains 60% by weight of lyophilized powder of cattle ehaculum, 30% by weight of grifola umbellata (CHULING Polyporus) and 10% by weight of papaya powder, is more effective in treatment of breast cancer, ovarian cancer and uterine cancer. As a specific case, Ms. Guo is a woman of 39 years old, who had been suffered from breast cancer, and extensive metastasis of the cancer occurred in ovaries after surgery treatment. After the treatment with the above compound anti-cancer capsule, the volume of tumor is reduced by more than one third, and she has lived healthy for almost 10 years up to now. There are about 50 similar cases in clinical tests, which comprise 15% of the treated patients.

4). Treatments of digestive system tumors (e.g. esophageal cancer, stomach cancer or colon cancer) resulted in the effective rate of 68%. As a specific case, Ms. Zhang is a woman farmer of 59 years old lived in SHANXI province of China. She had been suffered from esophageal cardiac cancer and received radical mastectomy in October 1991. From Nov. 3, 1992, the patient had encountered aggravated dysphagia. A subcostal 3×6 cm located mass was found by palpation and the patient was diagnosed as the recurrence of cardiac cancer. This patient is treated with the above compound anti-cancer capsule alone, without receiving radiation therapy or other chemotherapies. After a course of treatment, the symptom of dysphagia was eliminated and no undesirable effect was observed. She has lived normally up to now and even can work in the farm.

Treatments of respiratory system tumors (e.g. lung cancer) resulted in the effective rate of 63%. As a specific case, Mr. Shi is a lawyer of 60 years old. He had got a continuous high fever and began to encounter hemoptysis in March 1994, with a lump in the lung. On Apr. 8, 1994, he had been diagnosed as small cell lung cancer, which is not suitable to receive the surgery. Then, after a treatment with the formulation of the invention (XINXING No. I) of ten days, the symptoms of hemoptysis and fever were eliminated. After the treatment of 45 days, the lump in the lung was disappeared as monitored by X-ray photography. He has been working for a law form and being totally healthy up to now.

Furthermore, treatments of osteocarcinama resulted in the response rate of 61% (with reduced pain) and the cure rate of 14%. Treatments of leukemia resulted in the response rate of 61% and the cure rate of 11%.

In conclusion, the dosage forms of animal ejaculum of the present invention are effective in treatment of various diseases, including epilepsy, brain tumor, gynecological tumor, gastrointestinal tumor, respiratory cancer, liver tumor, lupus erythematosus, dermatosis, depression, Alzheimer's disease, blood diseases, etc.

Up to now, the preparation and use of ejaculum in treatment of diseases including cancers have not been reported. The present invention is novel and much valuable in the area of medicine and pharmacology.

The invention claimed is:

1. A medicinal material consisting of an animal ejaculum and erythorbate as an additive, wherein the medicinal material is suitable for oral administration alone or for the formulation of a pharmaceutical composition, the animal ejaculum is in the form of white powder, and the animal ejaculum is a vacuum lyophilized animal ejaculum.

2. The medicinal material according to claim 1, wherein the animal ejaculum is the ejaculum of cattle, horses, or donkeys.

* * * * *